(12) United States Patent
Bennett et al.

(10) Patent No.: US 12,128,412 B2
(45) Date of Patent: Oct. 29, 2024

(54) SPECIMEN CONTAINER FOR SPECIMEN PRE-PROCESSING

(71) Applicant: QUANTUMDX GROUP LIMITED, Tyne and Wear (GB)

(72) Inventors: James Bennett, Tyne and Wear (GB); Neil Litten, Reading (GB); Richard Smith, Sandy (GB); Julian Brandon-Jones, Whittlesford (GB)

(73) Assignee: QUANTUMDX GROUP LIMITED, Newcastle Upon Tyne (GB)

( * ) Notice: Subject to any disclaimer, the term of this patent is extended or adjusted under 35 U.S.C. 154(b) by 0 days.

(21) Appl. No.: 17/593,167

(22) PCT Filed: Mar. 9, 2020

(86) PCT No.: PCT/GB2020/050554
§ 371 (c)(1),
(2) Date: Sep. 10, 2021

(87) PCT Pub. No.: WO2020/183141
PCT Pub. Date: Sep. 17, 2020

(65) Prior Publication Data
US 2022/0184608 A1 Jun. 16, 2022

(30) Foreign Application Priority Data
Mar. 12, 2019 (GB) ..................................... 1903401

(51) Int. Cl.
*B01L 3/00* (2006.01)
*A61B 10/00* (2006.01)

(52) U.S. Cl.
CPC ........ *B01L 3/5029* (2013.01); *A61B 10/0096* (2013.01); *B01L 2300/042* (2013.01); *B01L 2300/0672* (2013.01); *B01L 2300/0832* (2013.01); *B01L 2400/0683* (2013.01)

(58) Field of Classification Search
CPC ............. B01L 3/5029; B01L 2300/042; B01L 2300/0672; B01L 2300/0832; B01L 2400/0683; A61B 10/0096
See application file for complete search history.

(56) References Cited

U.S. PATENT DOCUMENTS

| 4,184,483 A | 1/1980 | Greenspan |
| 4,353,868 A | 10/1982 | Joslin |
| 2006/0216196 A1 | 9/2006 | Satoh |

(Continued)

FOREIGN PATENT DOCUMENTS

| JP | 2014-502353 A | 1/2014 |
| WO | WO 95/25948 A1 | 9/1995 |

OTHER PUBLICATIONS

International Search Report and Written Opinion mailed on Apr. 15, 2020 in International Application No. PCT/GB2020/050554.

(Continued)

*Primary Examiner* — Samuel P Siefke
(74) *Attorney, Agent, or Firm* — Knobbe, Martens, Olson & Bear, LLP (57) ABSTRACT

A specimen container has a vessel having a reservoir and a specimen collection region. The specimen container also has a sleeve located within the vessel and moveable in the direction of the reservoir. Movement of the sleeve in the direction of the reservoir results in the specimen collection region and reservoir being brought into fluid communication with each other.

13 Claims, 8 Drawing Sheets

(56) References Cited

U.S. PATENT DOCUMENTS

| | | |
|---|---|---|
| 2009/0024055 A1 | 1/2009 | Nguyen |
| 2013/0092690 A1 | 4/2013 | Skakoon |
| 2013/0243669 A1 | 9/2013 | Baron et al. |

OTHER PUBLICATIONS

Office Action issued on Nov. 16, 2023 for Japanese Application No. JP 2021-554993, 6 pages.

SPECIMEN CONTAINER FOR SPECIMEN PRE-PROCESSING

PRIORITY AND CROSS REFERENCE TO RELATED APPLICATIONS

This application is the U.S. National Phase Application under 35 U.S.C. § 371 of International Application No. PCT/GB2020/050554, filed Mar. 9, 2020, designating the U.S. and published in English as WO 2020/183141 A1 on Sep. 17, 2020, which claims the benefit of Great Britain Application No. GB 1903401.6, filed Mar. 12, 2019. Any and all applications for which a foreign or a domestic priority is claimed are identified in the Application Data Sheet filed herewith and are hereby incorporated by reference in their entireties under 37 C.F.R. § 1.57.

FIELD

The present invention relates to a specimen container. More particularly but not exclusively, the present invention relates to a container for collecting a biological specimen prior to diagnostic testing.

BACKGROUND

Typically, before diagnostic tests can be performed on a biological specimen, a specimen must be collected from an individual. Depending on the biological specimen type, collection may involve the drawing of liquids such as blood or urine and directly aspirating, pipetting or pouring the specimen into a collection tube, or using a swab, such as a buccal swab and placing it into a specimen collection tube. In many cases the specimens are initially mixed with buffers. The buffers may help to dissolve or re-disperse the specimen and/or may include anticoagulants, preservatives or other materials.

The specimen is then typically further processed. Such steps may involve lysing cells, extracting and amplifying DNA and chemically stabilising the specimen prior to testing. More recently, point of care devices are being developed to carry out much of the specimen processing in an automated manner, however it is still necessary to collect the initial specimen in an appropriate manner to allow it to be easily transferred into the point of care device. It is important that specimen collection and processing is performed accurately and reliably to ensure the accuracy and reliability of diagnostic tests that are performed on the specimen.

Currently, much of the specimen collection and initial processing is performed manually by a user. Typically, manual specimen processing involves the user adding predetermined amounts of one or more fluids e.g. buffers to the specimen using a manual device such as a pipette. The specimen is then manually transferred for downstream processing such as diagnostic processing, which may more recently for example include loading the sample into a point of care testing device.

However, there are various disadvantages associated with current specimen collection and initial processing techniques. Most notably, they are often slow and prone to user error. Many of them also require access to specialist consumables and equipment as well as specially-trained users and, even when performed correctly, risk the user contacting infectious agents and potentially hazardous substances that can be present in certain buffer solutions.

These disadvantages make initial specimen collection and processing unsuited to point of care settings, which have limited access to specialist equipment and specially trained users. These disadvantages are especially relevant to point of care settings in low and middle income countries—where, conversely, there is often a particular need to provide accurate and low-cost diagnostic testing.

The present invention aims to obviate or mitigate one or more of these disadvantages.

SUMMARY

According to a first aspect of the present invention, there is provided a specimen container comprising a vessel, the vessel comprising a reservoir and a specimen collection region. The specimen container also comprises a sleeve located within the vessel, which is moveable in the direction of the reservoir. Movement of the sleeve in the direction of the reservoir results in the specimen collection region and reservoir being brought into fluid communication with each other.

Preferably the sleeve located within the vessel, is only moveable in the direction of the reservoir.

Advantageously this arrangement means that fluid, such as specimen processing fluid, can be stored in a sealed reservoir and subsequently a specimen such as a biological specimen can be introduced into the specimen collection region (typically a liquid or a swab) and selectively brought into fluid communication with fluid in the reservoir by actuating a moveable sleeve within the vessel. An effective, simple to operate, low cost device for processing a biological specimen is provided. The reservoir can remain sealed until the device is used. This means that the device can be stored for an extended period of time before use. The device is particularly suited to point of care applications due to its size, simplicity and the protection provided to the user.

Preferably the specimen container further comprises a lid adapted to make closing contact with the vessel.

Preferably, the lid comprises an outer wall shaped to correspond with a surface of the vessel to provide a fluid seal when the lid makes closing contact with the vessel.

Advantageously this arrangement means that a specimen can be sealed into the vessel. When sealed the vessel can provide for safer and/or longer storage of the specimen.

Preferably the lid is adapted to operably interact with the sleeve to move the sleeve in the direction of the reservoir when a mechanical force is applied to the lid as it makes closing contact with the vessel.

Advantageously as the manual force can be a manual mechanical force this is particularly useful in point of care situation where a user can simply manually close the lid.

Preferably, the lid comprises an inner wall shaped to operably interact with the sleeve.

Advantageously this arrangement means that the moveable sleeve member can be actuated when a compatible lid is applied without any further steps required by a user. This can further simplify the operation of the device. Further, in typical operation, fluid remains sealed in the reservoir until the lid has been secured. Thus, the risk of a user accidentally contacting fluid in the reservoir is reduced.

Advantageously the inner wall of the lid is configured such that it minimises accidental contamination risk from user touching or placing the lid on a dirty surface.

Preferably the sleeve has a first configuration in which movement towards the reservoir cannot occur, and a second configuration in which movement towards the reservoir can occur.

Preferably the sleeve is arranged such that it is biased towards the first configuration and is movable from the first configuration to the second configuration when it operably interacts with a compatible lid as the lid makes closing contact with the vessel.

Advantageously this means that actuation of the sleeve can be prevented until the sleeve interacts with a suitably-shaped lid. This can reduce the risk of a user accidentally moving the sleeve, thereby bringing the specimen collection region and reservoir into fluid communication.

Preferably the vessel comprises at least one abutment surface, and the sleeve comprises at least one leg portion arranged to contact the at least one abutment surface.

Advantageously this arrangement can effectively maintain the sleeve in the first configuration even when mechanical force is applied to the sleeve in the direction of the reservoir.

Preferably the at least one abutment surface comprises a ledge extending around at least part of an inner surface of the vessel.

Preferably in the first configuration the at least one leg portion is biased against the abutment surface such that movement of the sleeve in the direction of the reservoir cannot occur.

Preferably the sleeve comprises a plurality of spaced-apart leg portions.

Advantageously this arrangement ensures the sleeve can be maintained in the first configuration more securely.

Preferably the sleeve comprises at least one elongate member extending from the one or more leg portions towards the reservoir.

Preferably the sleeve comprises a plurality of elongate members separated by a plurality of sleeve apertures.

Advantageously this arrangement means that when the specimen container containing fluid is rotated by a user, the elongate members may act as baffles to increase mixing of the fluid.

Preferably the sleeve apertures are arranged such that after movement of the sleeve in the direction of the reservoir, the specimen collection region and reservoir are brought into fluid communication with each other via the sleeve apertures.

Advantageously, the sleeve apertures provide a fluid communication pathway that enables mixing of the specimen with fluid in the reservoir.

Preferably the sleeve comprises a surface located adjacent to an end of the at least one elongate member closest to the reservoir, the surface arranged to prevent fluid communication between the specimen collection region and the reservoir prior to movement of the sleeve in the direction of the reservoir.

Advantageously this arrangement provides a sleeve that functions as a "plunger" such that a surface of the sleeve seals the reservoir prior to movement of the sleeve, whilst after movement of the sleeve the surface moves into the reservoir such that fluid from the reservoir can then enter the sleeve and contact any sample therewithin.

Preferably, the shape of the sleeve is such that it seals the reservoir prior to movement and the shape of the reservoir is such that, after movement, fluid communication between the specimen collection region and the reservoir is enabled.

Preferably, there is a waist portion of the vessel between the reservoir and the specimen collection region, the waist portion being sized to sealably receive the surface of the sleeve that is arranged to prevent fluid communication.

Advantageously by having the circumference of the waist portion being narrower than the circumference of the reservoir this can assist with the initial locating of the sleeve in the vessel. There may also be a snap-fit/temporary mechanical fixing to aid the location and assembly of the parts. This restricts the movement in the opposing direction to the intended direction.

Preferably, the waist portion comprises an undercut section arranged to prevent or restrict the surface of the sleeve that is arranged to prevent fluid communication back into the specimen collection region.

Alternatively, the sleeve comprises a piercing member located adjacent to an end of the at least one elongate member closest to the reservoir, the piercing member arranged to pierce a seal of the reservoir on contact with the reservoir.

Advantageously, this provides a simple means with which the seal can be actuated to bring the specimen collection region and reservoir into fluid communication with each other.

Optionally, the reservoir comprises a pierceable seal. Said seal may comprise a foil material.

Optionally an outer surface of the specimen container comprises at least one shaped region for securing a lid to the specimen container.

Preferably the shaped region comprises a ridge or an indented region.

This arrangement enables a lid to be held securely on the specimen container. Furthermore, this can prevent a lid from being easily removeable by a user. This can prevent a user from removing the lid and accidentally contacting fluid in the container.

Preferably the reservoir contains a fluid.

Preferably the reservoir contains a predetermined volume of fluid.

Optionally, the reservoir could contain dried reagent.

Advantageously the amount of fluid in the reservoir can be measured with improved accuracy, for example during manufacturing. This can reduce the risk of user error during operation. This can also improve the accuracy of subsequent diagnostic tests performed on the specimen.

Optionally the fluid is a buffer fluid. The buffer fluid may be for stabilising a biological specimen.

Various further features and aspects of the invention are defined in the claims.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Figure 1A:
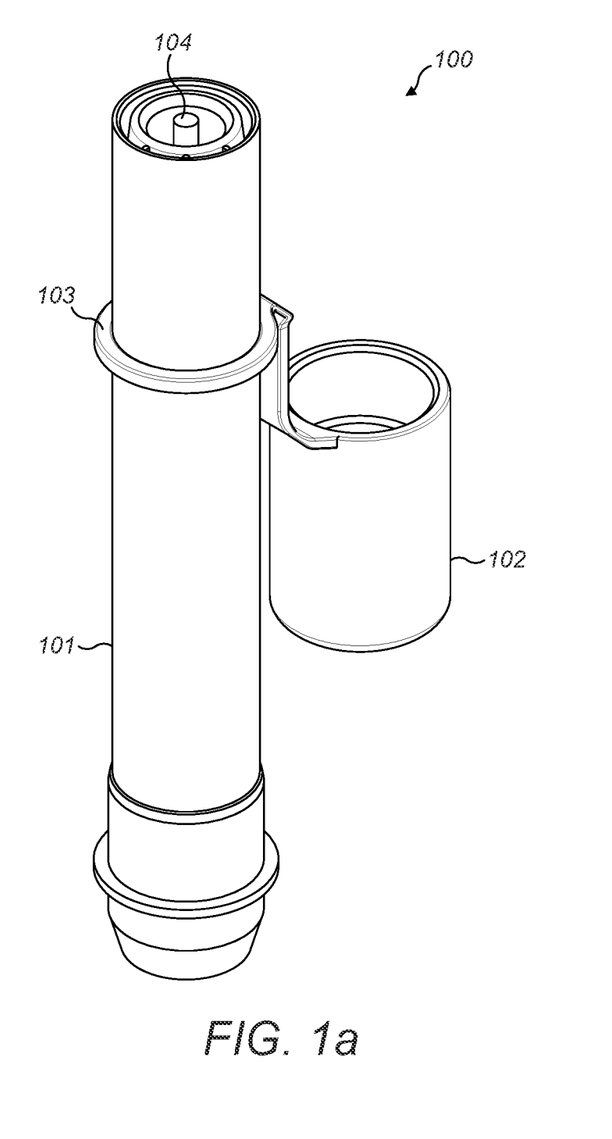
FIG. 1a provides a schematic diagram of a specimen container before a lid has been attached.

FIG. 1a shows a specimen container 100 according to certain embodiments of the present invention. The specimen container 100 includes a vessel 101. The specimen container also includes a lid 102 which in FIG. 1a has not yet been attached to (and thereby made closing contact with) the vessel 101. In this embodiment, the lid 102 is held to the vessel 101 by a lid retaining member 103. The lid retaining member 103 allows the lid 102 to be attached to the vessel 101 but prevents it from being lost by a user.

In an alternative embodiment, often preferred, the lid is not held to the vessel by a lid retaining member and is simply provided as a separate lid either, as part of a kit or separately.

A swab 104 containing a biological specimen is located inside the vessel 101. The swab 104 has been introduced into the vessel 101 by a user for processing.

Figure 1B:
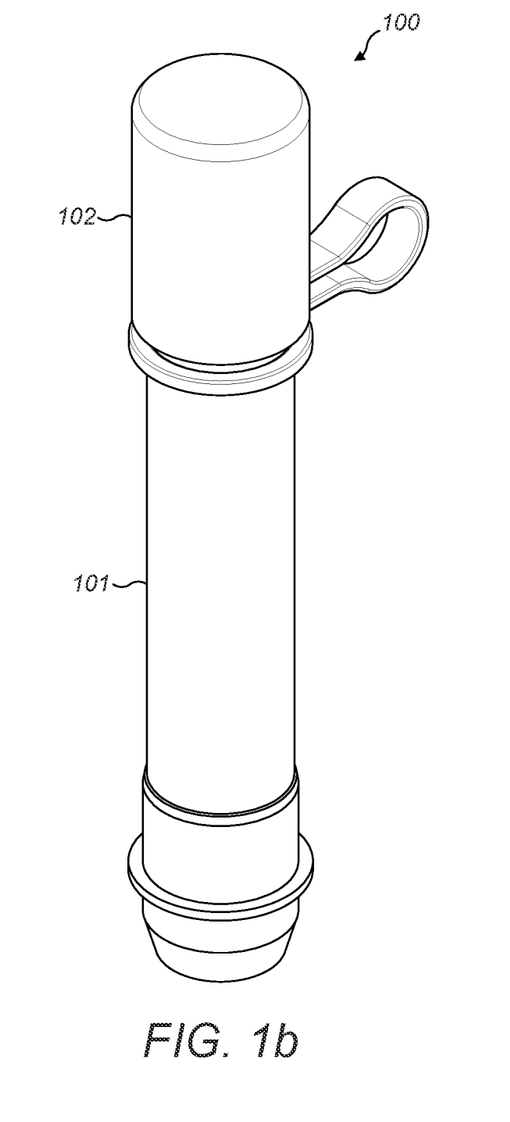
FIG. 1b provides a schematic diagram of the specimen container of FIG. 1a after a lid has been attached.

FIG. 1b shows the specimen container 100 of FIG. 1a after the lid 102 has been attached to the vessel 101.

Figure 2:
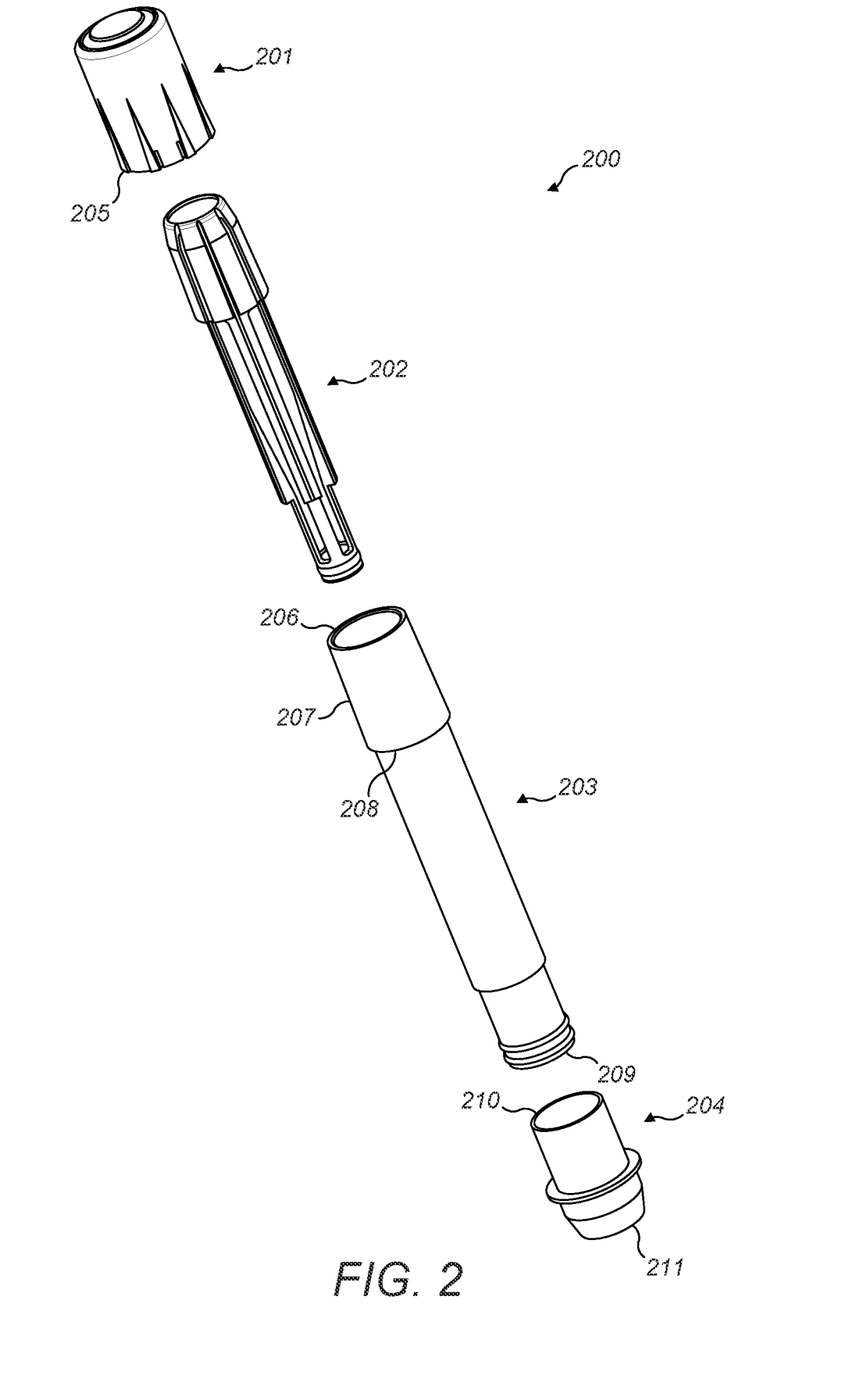
FIG. 2 provides a schematic exploded diagram of components of a specimen container.

FIG. 2 shows an exploded view of a specimen container 200 according to certain embodiments of the present invention. The specimen container includes a lid 201, a sleeve 202, a vessel 203 and a base component 204.

The lid 201 is adapted to make closing contact with the vessel 203. The lid 201 includes an outer wall 205 that is shaped to correspond with an outer surface 207 of the vessel 203 adjacent to a first end 206 of the vessel 203 such that fluid in the vessel 203 is prevented from leaving the first end 206. The lid 201 also includes an inner wall shaped to operably interact with the sleeve 202 as the lid 201 is secured to the vessel 203. The configuration of the lid 201 and the operable interaction between the lid 201 and the sleeve 202 is described in more detail below.

The sleeve 202 is shaped such that it can move within the vessel 203 when mechanical force is applied to it. The sleeve 202 has a first configuration in which movement within the vessel 203 in the direction of the base component 204 is prevented (generally depicted in FIG. 5a). Movement of the sleeve in the opposite direction, i.e. away from the base component 204, is also restricted as the sleeve 202 includes a first end 301 and a second end 302, and the second end 302 is retained in the vessel by a snap-fit undercut 315 (as shown in FIG. 6) located between the specimen collection region and the reservoir, sized to retain a base surface 313 of the sleeve 202 in the vessel 203. The undercut 315 allows insertion of the sleeve 202 during manufacture but then acts to prevent the sleeve 202 being removed from the vessel 203.

In this first configuration the sleeve 202 is located within the vessel 203 such that it cannot easily be accessed by a user. The sleeve 202 also has a second configuration in which movement within the vessel 203 in the direction of the base component 204 is possible (generally depicted in FIG. 5b). The sleeve 202 includes an inner aperture extending through the inside of the sleeve 202 to allow a swab or fluid specimen to be introduced into the sleeve 202. The configuration of the sleeve 202 is described in more detail with reference to FIG. 3.

The vessel 203 includes a first end 206 and a second end 209. The vessel 203 also includes an inner region adjacent to the first end 206 defining a specimen collection region. The specimen collection regions allows a biological specimen such as a swab or a fluid to be introduced into the vessel 203 via the first end 206.

The vessel 203 includes an inner surface extending between the first end 206 and second end 209. The inner surface is shaped to cooperate with the sleeve 202. The inner surface includes an abutment surface arranged to cooperate with surfaces of the sleeve 202 when the sleeve 202 is in the first configuration. The abutment surface is a ledge extending circumferentially around at least part of the inner surface of the vessel 203.

The vessel 203 includes an outer surface 207. A region of the outer surface 207 adjacent to the first end 206 is shaped to cooperate with an inner surface of the outer wall 205 of the lid 201 to make a fluid-tight seal, along with the outer surface of the inner wall, when the lid 201 is attached to the first end 206. The outer surface 207 of the vessel 203 includes a shaped region 208 which in this embodiment comprises a ridge extending around the circumference of the vessel 203. The shaped region 208 is arranged such that it cooperates with the lid 201 to prevent the lid 201 from being removed from the vessel 203 by a user after it has been secured. In this example, the inner surface of the outer wall 205 of the lid 201 includes one or more surfaces that engage with the shaped region 208 when the lid has been fully secured.

The base component 204 includes a first end 210. The base component 204 also includes an inner region adjacent to the first end defining a reservoir. The reservoir is arranged to contain a pre-determined volume of fluid used for processing a biological specimen. The base component 204 includes a second end 211. The second end 211 includes a seal 212 (shown in FIG. 6) to prevent fluid from leaving the reservoir via the second end 211. In this embodiment, the seal 212 is a re-piercable, self-sealing membrane or septum seal that allows a needle to be inserted to draw fluid from the reservoir and which will then re-seal when the needle is removed.

In this embodiment the base component 204 is provided as a separate part that is attached to the second end 209 of the vessel 203 during manufacturing via suitable fluid-tight securing means. However, in certain embodiments the base component 204 can be integrally formed with the vessel 203.

Figure 3:
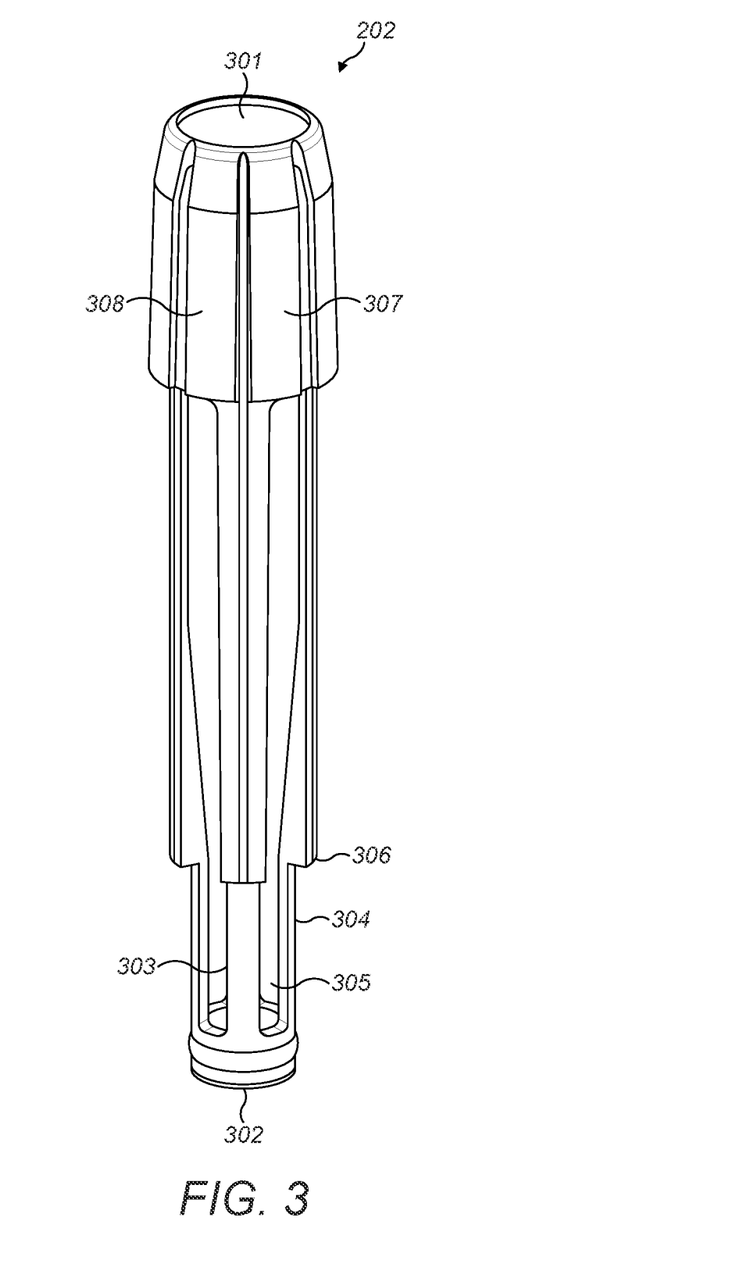
FIG. 3 provides a more detailed view of the sleeve of FIG. 2.

The sleeve 202 will now be described in more detail with reference to FIG. 3.

The sleeve 202 includes a first end 301 and a second end 302. The sleeve 202 also includes a plurality of elongate members extending between the first 301 and second 302 end. In the embodiment depicted in FIG. 3, the sleeve 202 includes four elongate members. However, it will be appreciated that more or fewer elongate members could be provided.

The elongate members are separated by sleeve apertures. For example, first 303 and second 304 elongate members are separated by first sleeve aperture 305. The sleeve apertures are arranged to provide a fluid communication passageway such that fluid can enter the inside of the sleeve 202.

Typically, a shaped region 306 is located part way along the length of at least one of the elongate members. The shaped region 306 is arranged to contact a corresponding inner surface of the vessel 203 such that movement of the sleeve within the vessel is prevented beyond a predetermined position.

The sleeve 202 includes a central aperture extending through the inside of the sleeve 202 from the first end 301 towards the second end 302. The aperture is shaped such that a specimen such a blood, tissue etc or a swab or other material can be inserted into the first end 301 of the sleeve 202 via the aperture.

The sleeve 202 includes a base element 313 secured to or integrally formed with the end of the elongate members adjacent to the second end 302 of the sleeve 202. The base element 313 includes a surface that is shaped to cooperate with a corresponding surface of the vessel 314 to create a fluid tight seal between the specimen collection region and the reservoir prior to movement of the sleeve 202 within the vessel.

In this embodiment, the surface is a substantially circular base surface 313 and the inner surface of the vessel includes a similarly-shaped sealing region 314. Prior to movement of the sleeve, the surface of the sleeve and the sealing region of the vessel are arranged to create a fluid-tight seal such that fluid cannot pass between the reservoir and the specimen collection region. After movement, the surface of the sleeve moves down into the reservoir. The reservoir is shaped such that that the seal is broken. Typically, the reservoir has a larger diameter than the sealing region of the vessel.

The sleeve 202 also includes a plurality of spaced-apart leg portions adjacent to and extending out from the first end 301. In the embodiment shown in FIG. 3, the sleeve 202 includes six leg portions including first leg portion 307 and second leg portion 308. However, it will be appreciated that more or fewer leg portions could be provided.

The leg portions extend downwardly and outwardly from the first end 301 such that a gap is formed between the leg portions and the remainder of the sleeve 202 when the sleeve 202 is located within the vessel 203.

When the sleeve 202 is located within the vessel 203, the leg portions are mechanically biased away from the longitudinal axis of the sleeve 202.

In the first configuration of the sleeve 202, the leg portions are biased against the abutment surface of the vessel 203. This prevents movement of the sleeve 202 towards the reservoir. In the second configuration, the leg portions are translated inwardly (i.e. towards the sleeve) such that they are no longer biased against (and no longer contact) the abutment surface. This allows movement of the sleeve towards the reservoir. In this way, the sleeve 202 is biased towards the first configuration and movable from the first configuration to the second configuration when it operably interacts with the lid 201.

Whilst in the embodiment shown the abutment surface extends completely around the circumference such that the leg portions 307, 308 etc. must be radially drawn in by the lid 201 to allow the sleeve to then move towards the reservoir it would be appreciated that the abutment surface could be provided as portions with gaps therebetween and the lid in this case could act to rotate the sleeve such that it moves from axial alignment with the abutment surface whereby movement is prevented to axial alignment with the gaps where movement is allowed.

It will be appreciated that different configurations of sleeve can be provided. For example, in certain embodiments, the sleeve comprises a piercing member located adjacent to an end of at least one elongate member and the reservoir is sealed by a pierceable seal. Typically, in this embodiment the seal is composed of a foil material. On movement of the sleeve, the piercing member contacts and breaks the seal thereby bringing the specimen collection region and reservoir into fluid communication.

Figure 4:
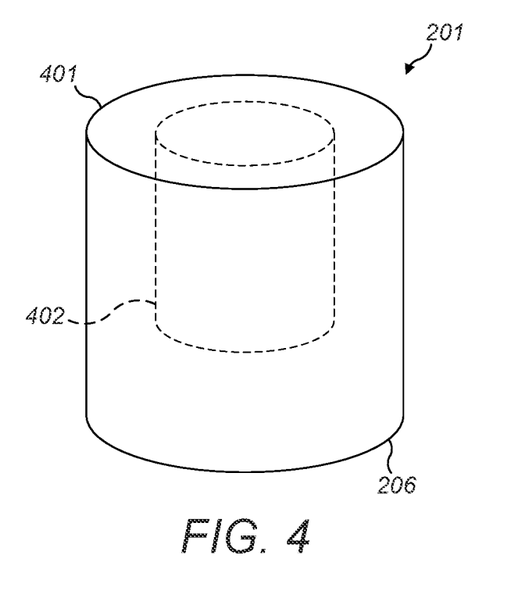
FIG. 4 provides a more detailed cross-sectional view of the lid of FIG. 2.

The lid 201 will now be described in more detail with reference to FIG. 4. The lid 201 is adapted to make closing contact with the vessel. The lid 201 includes an outer wall 205 that is shaped to correspond with the outer surface of the vessel adjacent to the first end of the vessel. In embodiments where a cylindrical vessel is used, the outer wall 205 is substantially cylindrical in shape.

The lid 201 also includes an inner wall 402. An outer surface of the inner wall is shown in FIG. 4. The inner wall 402 is shaped to operably interact with the sleeve 202 as the lid 201 is secured to the vessel 203. Typically, the inner wall 402 is also substantially cylindrical in shape and has a smaller diameter than the outer wall 205. The outer wall to some extent acts to protect the inner wall from potential contamination by minimising the likelihood that it would come into contact with the user and ensuring it would not make contact with potentially dirty or contaminated surfaces if placed down by the user. The inner wall 402 is shaped to contact the legs of the sleeve 202 as the lid 201 is secured to the vessel. As the inner wall 402 contacts the legs of the sleeve 202, the legs move from the first configuration to the second configuration to allow movement of the sleeve towards the reservoir of the base component 204.

Figure 5A:
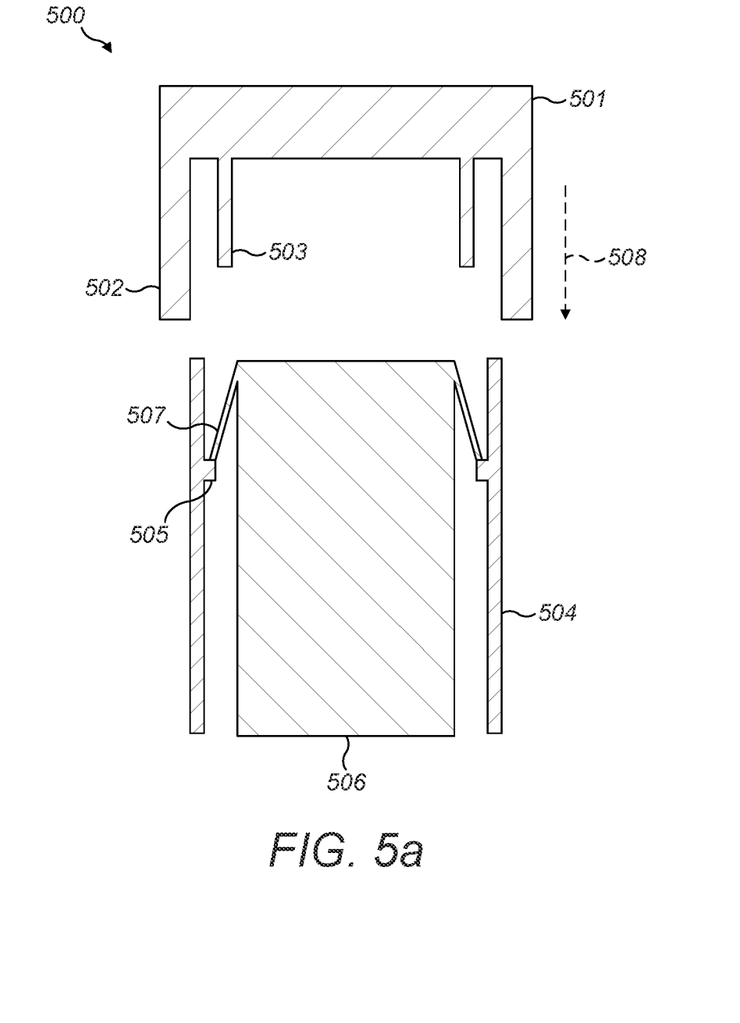
FIG. 5a provides a schematic cross-sectional diagram of a specimen container before a lid is attached.
Figure 5B:
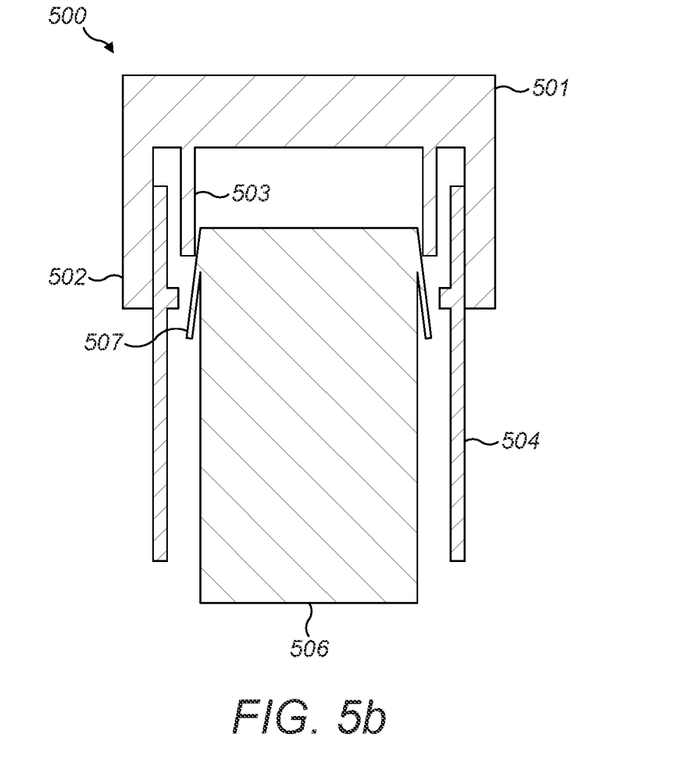
FIG. 5b provides a schematic cross-sectional diagram of the specimen container of FIG. 5a as a lid is attached.
Figure 6:
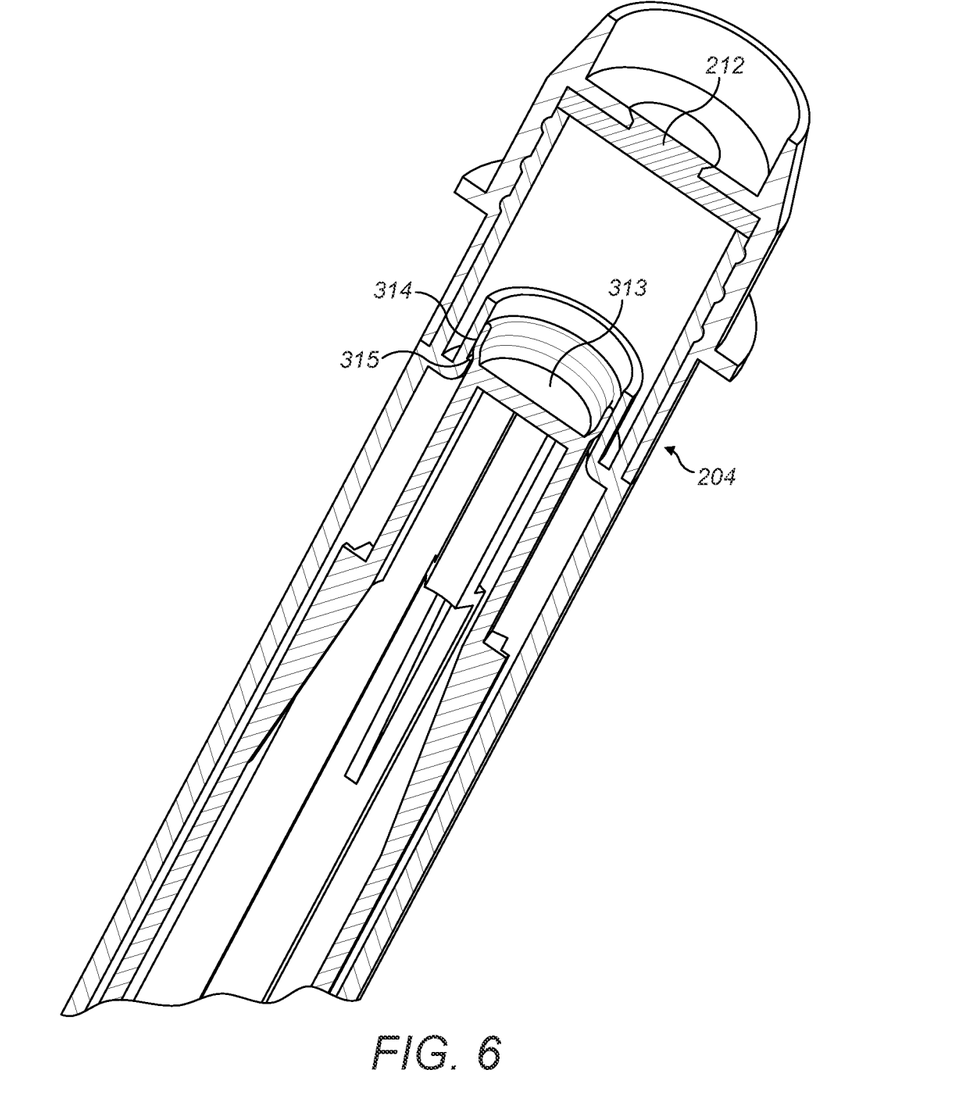
FIG. 6 provides a schematic cross-sectional diagram of a portion of the specimen container.

FIGS. 5*a* and 5*b* provide a simplified cross-sectional view of a specimen container 500 according to certain embodiments of the present invention. The specimen container 500 is shown in a first configuration in FIG. 5*a* and a second configuration in FIG. 5*b*.

As described herein, the specimen container 500 includes a lid 501 including an inner wall 503 and outer wall 502. Also shown are a vessel 504 including an abutment surface 505, and a sleeve 506 including a plurality of leg portions 507. The direction of movement of the lid 501 as it is inserted onto the vessel is shown by dashed arrow 508.

Prior to use, the specimen container 500 is assembled into a ready-to-use condition. The sleeve is inserted into the vessel 504 into the first configuration as shown in FIG. 5*a*. The reservoir is then filled with a predetermined volume of fluid. If a separate base component is used, the base component is then secured to the vessel.

In the first configuration, the leg portions 507 are biased against the abutment surface 505 of the sleeve 506. As a result, the sleeve 506 is prevented from moving within the vessel 504 in the direction of the reservoir even when mechanical force is applied by a user.

Typically, the specimen container 500 is assembled into the ready-to-use condition during the manufacturing process although alternatively some or all of the assembly steps could be performed by the user at the time of use.

The user takes a specimen from a patient. In this example the specimen is taken using a swab. The user then inserts all or part of the swab into the specimen collection region adjacent to the first end of the vessel. It would be understood that the stem of the swab could be breakable to allow the end of the swab with the specimen to be removed and retained in the vessel. A specimen container 100 with a swab inserted is shown in FIG. 1.

Next, the user attaches the lid 501 to the vessel 504 by locating the lid 501 over the vessel 504 and applying a mechanical force in the direction denoted by dashed arrow 508.

As shown in FIG. 5*b*, as the lid 501 is inserted, the inner wall 503 of the lid 501 contacts the leg portions 507. The contact moves the leg portions 507 inwards towards the sleeve 506 which then assumes the second configuration. In the second configuration, the leg portions 507 do not contact the abutment surface. This means that the sleeve 506 can move within the vessel 504 towards the reservoir.

The user continues to apply mechanical force to the lid 501 until the lid 501 is fully inserted onto the vessel 504. In the fully inserted position, the lid 501 is secured to the vessel 504 via a fluid-tight seal and the sleeve 506 has moved within the vessel 504 such that the specimen collection region and reservoir are in fluid communication. As described above, typically once sealed, the lid 501 and the vessel 504 are arranged such that the lid 501 cannot be mechanically removed by a user. This results from the snap-fit of the lid 501 onto the vessel which actuates with an audible click upon final engagement.

After the lid 501 has been secured to the vessel 504, the user agitates and/or rotates the specimen container 500 such that the specimen mixes with fluid contained in the reservoir. Advantageously, as the sleeve is not solid, i.e. it has one or more sleeve apertures 305, adequate mixing can usually be obtained by relatively gentle rotation, avoiding undesirable bubble formation than can occur with the more vigorous shaking typically instructed for mixing specimens with buffers in standard collection tubes. Once mixed, fluid in the specimen container 500 can be used for diagnostic testing, typically by inserting a needle into a septum seal located adjacent to a base surface of the reservoir and drawing fluid from the reservoir.

After mixing, the fluid can be stored in the sealed specimen container 500 for an extended period of time. This is advantageous because as several millilitres of sample can be stored i.e. more than is required for a single test, fluid can be re-drawn, for example in case of a failed diagnostic test, for carrying out an alternative test using the same specimen e.g. an STI test as well as an HPV test, or for quality control purposes.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope of the present disclosure. Accordingly, the various embodiments disclosed herein are not intended to be limiting, with the true scope being indicated by the following claims.

What is claimed is:

1. A specimen container comprising:
   a vessel comprising a reservoir and a specimen collection region; and
   a sleeve located within the vessel and configured to move in a direction of the reservoir; and
   a lid for the vessel;
   wherein the vessel and sleeve are configured to bring the specimen collection region and the reservoir into fluid communication with each other with movement of the sleeve in the direction of the reservoir,
   wherein the sleeve has a first configuration in which movement towards the reservoir cannot occur, and a second configuration in which movement towards the reservoir can occur, wherein the sleeve is arranged such that it is biased towards the first configuration, and
   wherein the lid is configured to contact and deform an integral portion of the sleeve to switch the sleeve from the first configuration to the second configuration with insertion into the vessel,
   wherein the integral portion of the sleeve comprises an outwardly extending leg portion configured to rest against an interior surface of the vessel in the first configuration,
   wherein the lid is configured to depress the leg portion during insertion into the vessel to switch the sleeve from the first configuration to the second configuration, and
   wherein the interior surface of the vessel comprises at least one protruding abutment surface and the leg portion is arranged to rest on the at least one abutment surface in the first configuration.

2. The specimen container of claim 1, wherein the lid is configured to make a closing contact with the vessel.

3. The specimen container of claim 2, wherein the lid is adapted to operably interact with the sleeve to move the sleeve in the direction of the reservoir when a mechanical force is applied to the lid as it makes closing contact with the vessel.

4. The specimen container of claim 1, wherein the integral portion of the sleeve comprises a plurality of spaced-apart leg portions.

5. The specimen container of claim 1, wherein the sleeve comprises at least one elongate member extending from the one or more leg portions towards the reservoir.

6. The specimen container of claim 5, wherein the sleeve comprises a plurality of elongate members separated by a plurality of sleeve apertures.

7. The specimen container of in claim 5, wherein the sleeve apertures are arranged such that after movement of the sleeve in the direction of the reservoir, the specimen collection region and reservoir are brought into fluid communication with each other via the sleeve apertures.

8. The specimen container of claim 1, wherein the sleeve comprises a surface located adjacent to an end of the at least one elongate member closest to the reservoir, the surface arranged to prevent fluid communication between the specimen collection region and the reservoir prior to movement of the sleeve in the direction of the reservoir.

9. The specimen container of claim 5, wherein the sleeve comprises a piercing member located adjacent to an end of the at least one elongate member closest to the reservoir, the piercing member arranged to pierce a seal of the reservoir on contact with the reservoir.

10. The specimen container of claim 1, wherein an outer surface of the specimen container comprises at least one shaped region for securing a lid to the specimen container.

11. The specimen container of claim 1, wherein the vessel has a waist portion between the reservoir and the specimen collection region, the waist portion being sized to sealably receive a lower surface of the sleeve, said sleeve being arranged to prevent fluid communication back into the specimen collection region.

12. The specimen container of claim 11, wherein the waist portion comprises an undercut section arranged to prevent or restrict the surface of the sleeve that is arranged to prevent fluid communication back into the specimen collection region.

13. The specimen container of claim 1, wherein the reservoir contains a fluid.

* * * * *